(12) United States Patent
Ogilvie et al.

(10) Patent No.: US 7,641,696 B2
(45) Date of Patent: Jan. 5, 2010

(54) CARPOMETACARPAL JOINT PROSTHESIS

(75) Inventors: William F. Ogilvie, Austin, TX (US);
Charles W. Mumme, Austin, TX (US);
Ian A. Trail, Wigan (GB)

(73) Assignee: Ascension Orthopedics, Inc., Austin, TX (US)

( * ) Notice: Subject to any disclaimer, the term of this patent is extended or adjusted under 35 U.S.C. 154(b) by 781 days.

(21) Appl. No.: 10/753,108

(22) Filed: Jan. 6, 2004

(65) Prior Publication Data

US 2005/0033426 A1 Feb. 10, 2005

Related U.S. Application Data

(60) Provisional application No. 60/438,487, filed on Jan. 7, 2003.

(51) Int. Cl.
*A61F 2/42* (2006.01)
(52) U.S. Cl. ................................. 623/21.15
(58) Field of Classification Search .............. 623/16.11, 623/21.11, 21.15
See application file for complete search history.

(56) References Cited

U.S. PATENT DOCUMENTS

| | | | |
|---|---|---|---|
| 5,358,529 A | 10/1994 | Davidson ..................... 623/20 |
| 5,405,400 A * | 4/1995 | Linscheid et al. ......... 623/21.15 |
| 5,645,605 A | 7/1997 | Klawitter .................. 623/21.15 |
| 5,938,700 A * | 8/1999 | Lippincott, III .......... 623/21.15 |
| 6,159,247 A * | 12/2000 | Klawitter et al. ......... 623/21.15 |
| 6,217,616 B1 | 4/2001 | Ogilvie ..................... 623/20.11 |
| 6,699,292 B2 | 3/2004 | Ogilvie et al. ........... 623/21.15 |
| 2002/0111691 A1 | 8/2002 | Wang et al. ............... 623/22.32 |
| 2005/0119757 A1* | 6/2005 | Hassler et al. ........... 623/21.15 |

* cited by examiner

*Primary Examiner*—William H. Matthews
*Assistant Examiner*—Jonathan Stroud
(74) *Attorney, Agent, or Firm*—Fitch, Even, Tabin & Flannery

(57) ABSTRACT

Hemi joint replacements for the base of the first metacarpal of the CMC joint are provided which can effectively restore and reestablish functional joint mechanics while preserving the soft tissues that contribute to joint stability and function. The implants have a unique head shape with a saddle-like articular surface that is shaped somewhat similar to a conventional bicycle seat. A set of four proportionately larger and smaller implants allows a surgeon to choose the appropriately sized prosthesis for implantation in respect of the metacarpal osteotomy.

14 Claims, 2 Drawing Sheets

CARPOMETACARPAL JOINT PROSTHESIS

This application claims priority from U.S. provisional application Ser. No. 60/438,487, filed Jan. 7, 2003, the disclosure of which is incorporated herein by reference. The present invention relates to a prosthesis for the carpometacarpal (CMC) joint.

BACKGROUND OF THE INVENTION

Overall, the design and manufacture of a functional, robust, and durable joint prosthesis is a complex and multifaceted problem involving anatomical, biocompatibility, biomechanical, and surgical considerations. From a functional perspective, mechanical design considerations should address the joint range of motion, center of rotation, force-transmission-capabilities, and wear resistance of the component. Anatomical issues for consideration involve the shape of the intramedullary stem and of the articulating surface, and the need for a range of sizes to accommodate anthropomorphic variations. Surgical concerns should take into account the need for appropriate instrumentation utilized during the implantation procedure to facilitate an accurate osteotomy, effect minimal bone removal, and preserve surrounding soft tissues. Generally, the design objective for such an implant to replace the distal articular surface of a diseased and/or damaged CMC joint should be to relieve pain, allow maximum range of motion, and restore to the patient a high degree of hand functionality. Size and geometric features of the component are in a large way dictated by morphometric measurements of the natural CMC joint; however, the strength and wear resistance of the ultimate component need to be such that it will exhibit longevity when subjected to rigorous and demanding anatomically relevant constraint and loading situations.

SUMMARY OF THE INVENTION

A pyrocarbon finger implant has now been developed for use as a hemi joint replacement for the base of the first metacarpal of the carpometacarpal (CMC) joint. Overall it comprises a one component prosthesis having a saddle configuration articular surface, resembling that of a conventional bicycle seat, which bears against the mating natural saddle surface of the trapezium. The particular saddle design allows for both flexion-extension joint motion and abduction-adduction motion. The opposite end of the implant has an anatomic intramedullary stem designed to be press-fit in place and to achieve fixation by means of implant/bone apposition (osseous integration). The prosthesis is preferably constructed of a machined graphite substrate which is encased within a thick layer of pyrocarbon. The provision of a matched set of proportional implants affords the surgeon to make a final decision in the midst of the ongoing surgery.

In a particular aspect, the invention provides a hemi joint replacement implant for the base of the first metacarpal of the CMC joint, which implant has a head section and a stem section, said head section having a flat distal collar surface from which the stem extends, and also having a saddle-shaped proximal articular surface, said proximal surface being convex in a lateral plane and concave in a dorsal-volar plane.

In another particular aspect, the invention provides a set of hemi joint replacement implants for the base of the first metacarpal of the CMC joint, each of said implants in said set having a head section and a stem section, with the head section having a flat distal collar from which the stem extends and also having a saddle-shaped proximal articular surface, said articular surface being convex in a lateral plane and concave in a dorsal-volar plane, and said plurality of replacement implants having heads which vary in height from about 11 mm to about 17 mm and in width from about 9 mm to about 15 mm, with the width always being between about 82% and about 87% of the height of the head section.

DETAILED DESCRIPTION OF THE PREFERRED EMBODIMENT

Figures 1, 2:
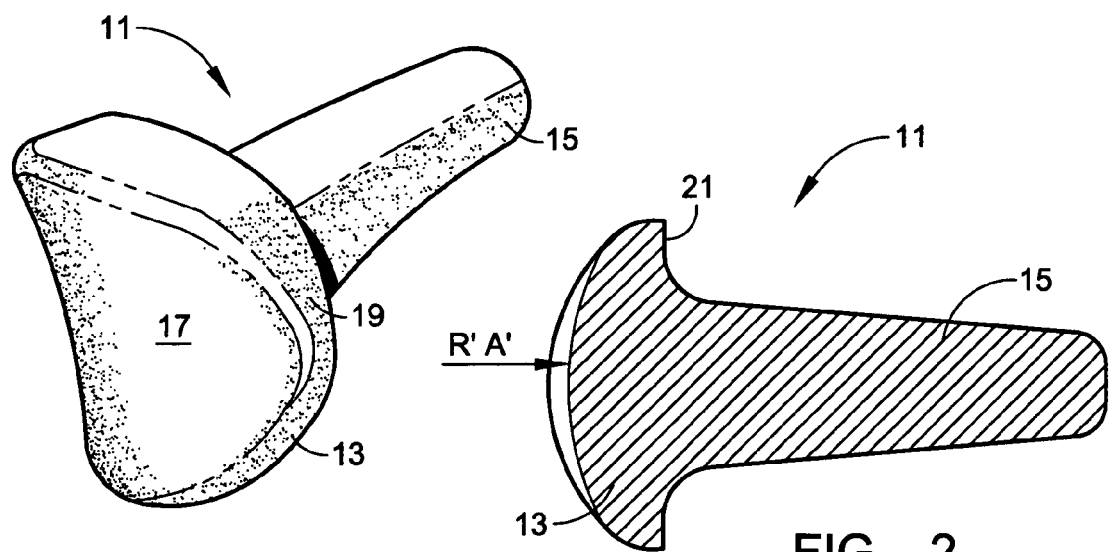
FIG. 1 is a perspective view illustrating a hemi CMC joint replacement implant.
FIG. 2 is a horizontal cross-sectional view of the prosthesis shown in FIG. 1 taken generally along the lines 2-2 of FIG. 3.

FIG. 1 illustrates a prosthesis 11 having an articular head 13 which embodies the preferred saddle design; an intramedullary stem 15 of the prosthesis extends to the right from the rear or distal surface of the head. The prosthesis 11 is designed to be implanted in the medullary canal of the first metacarpal after removing the base of that bone. By providing the implant 11 in four sizes, it is expected that the full range of the human anatomy will be covered.

For constructing the implant 11, it has been found that the combination of a machined graphite substrate which is coated overall with a completely encasing pyrocarbon layer is the preferred solution to meet the demands to which such an implant will be subjected. The pyrocarbon layer encases the graphite substrate and thus provides the external surface of the implant which interfaces with bone and soft tissues. Pyrocarbon exhibits a number of attributes deemed very desirable for an orthopedic prosthesis. These characteristics include: (1) high strength, (2) high wear resistance, (3) resistance to cyclic fatigue, (4) biocompatibility (with both blood and bone), (5) a modulus of elasticity similar to cortical bone, (6) an ability to support direct bone apposition, and (7) low friction on polished surfaces (e.g. coefficient of friction about 0.15). Although various medically approved dense pyrocarbons may be used, such as that sold under the trademark Pyrolite, pyrocarbon that is made in accordance with the teachings of U.S. Pat. No. 5,677,061 is particularly preferred; such is commercially available as On-X pyrocarbon.

The pyrocarbon layer, which completely encapsulates the graphite substrate, differs from it in mechanical properties; pyrocarbon is both stiffer and more fracture-resistant than graphite. As a result, the exterior pyrocarbon layer dominates the mechanical and biocompatibility characteristics of the components and provides the desired strength, durability, extreme resistance to wear, and both biological and biomechanical compatibility. Because pyrocarbon is not easily visible on radiographs, the graphite substrate is preferably machined from a material that is impregnated with a small amount of tungsten, e.g. 10 weight percent which is approximately 1 atomic percent; this renders the graphite substrate radiopaque and thus clearly visible on radiographs.

More specifically, the implant 11 consists of the articular head portion 13 and the stem portion 15. The front or proximal articular surface 17 of the articular head portion 13 has a saddle shape and is polished to a mirror finish so as to have an average surface roughness of about 8 microinches or less, e.g. an $R_A$=5.7±2.3 microinch (145±59 nm). In the presence of a lubricating medium, such as synovial fluid, such a mirror finish results in very low friction during articulation. Conversely, the stem portion 15 of the implant is not polished and may have a surface finish of essentially that produced during the pyrocarbon layer fabrication process, e.g. approximately 15 microinch (389 nm). The stem 15 preferably has a matte appearance and possesses a surface structure capable of achieving direct bone apposition.

By saddle surface is meant a surface that has a convex radius of curvature RA in the lateral plane through the anatomic center of rotation and a concave radius of curvature B in the central dorsal-volar plane. RA (see FIG. 2) is referred to as the adduction/abduction radius, and RB (see FIG. 3) as the flexion/extension radius. It will be understood that these radii will both increase in length from the smallest size implant that is provided to the largest; however, it is important that the increases are substantially proportionate in order to assure the desired improvement in overall function. It has been found that RB should be equal to about 125%±5% of the length of RA; preferably, it should be equal to 125%±1% thereof to assure the improved functioning is obtained.

Figures 3, 4:
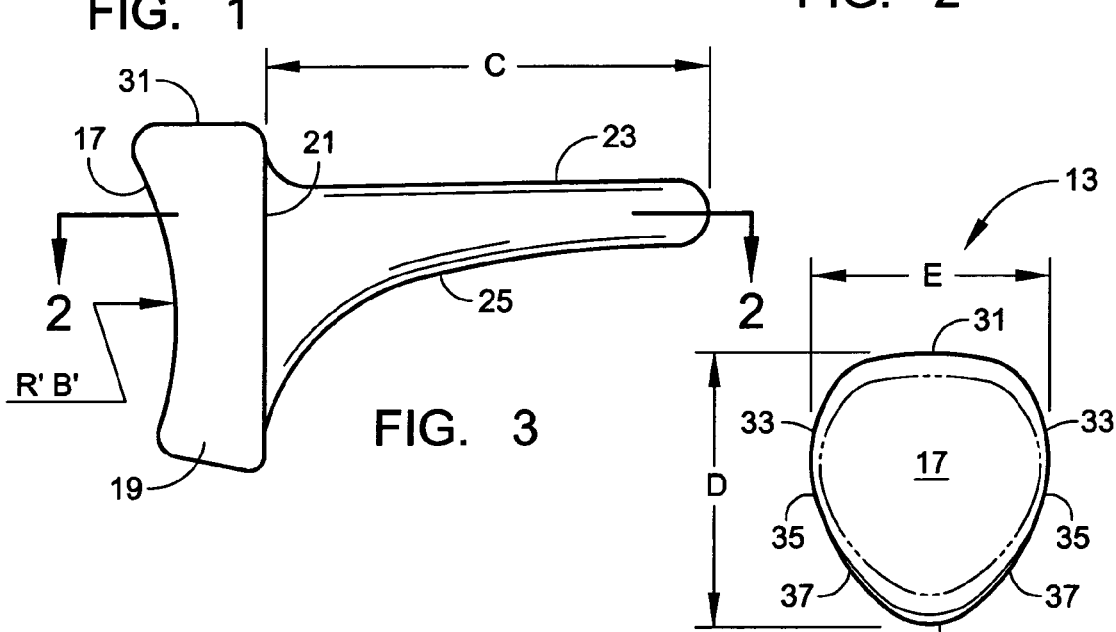
FIG. 3 is a right side view of the prosthesis of FIG. 1.
FIG. 4 is a front view of the prosthesis of FIG. 1.

The proximal articular surface 17 of the implant head is surrounded by a peripheral encircling surface 19 that extends between it and a distal surface in the form of a sub-articular collar 21 which, as shown in FIG. 3, is planar. The planar collar 21, which substantially encircles the anterior aspect of stem 15, simplifies the surgical technique required to implant the prosthesis, allowing for the use of alignment and cutting guides with a planar surface to properly prepare the bone so that it mates congruently with the planar sub-articular collar of the implant and thus provides a robust load transmission path. Moreover, the shape of the head (see FIG. 4), which is generally that of a bicycle seat, is designed to preserve the ligaments and the tendon attachments on the base of the 1$^{st}$ metacarpal while replacing articular cartilage, and to avoid impingement of the head against the base of the 2$^{nd}$ metacarpal and the lesser trapezoid bone during articulation of the joint.

It has been discovered that by producing implants in just four different sizes of carefully chosen proportions, the need for such prostheses of essentially all of the population can be fulfilled. The stem portion 15 is designed to conform generally to the anatomic shape of the medullary canal of the metacarpal bone in order to efficiently fill the canal and promote component fixation. The stem 15 is generally trapezoidal in cross section, with the wider base of the trapezoid being oriented toward the volar aspect of the canal. The width of the stem 15 tapers from a broad portion at the sub-articular collar 21 (see FIG. 2) to a narrower portion at the stem tip, and its length is designed to fill approximately ½ the length of the medullary canal of the 1$^{st}$ metacarpal (see dimension C in FIG. 3). In the four sizes of implants that have been designed, this dimension may vary from about 16 mm to about 23 mm. When viewed from the right side of the implant, i.e., in the medial-sagittal plane (see FIG. 3), the stem 15 has a straight dorsal surface 23 and a curved volar surface 25, with the stem tapering from the anterior aspect (collar) to the posterior aspect (tip or distal end). The stem also tapers radially; it is wide at the collar and narrow at the tip, as can be seen from FIGS. 2 and 3.

Figures 5, 5A:
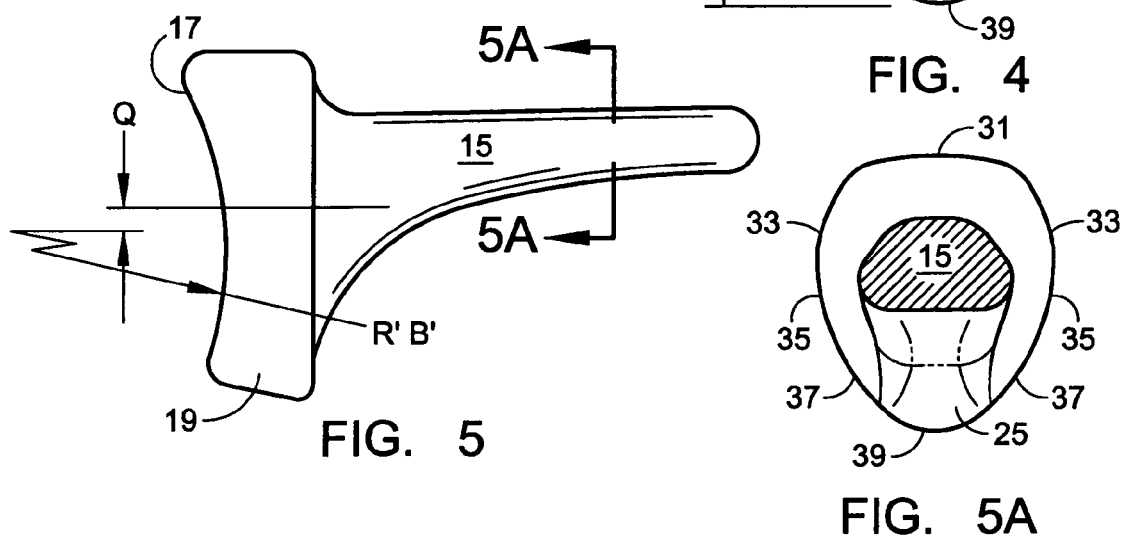
FIG. 5 is a view similar to FIG. 3, but reduced in size, which shows the location of a radius of curvature on the articular surface of the prosthesis of FIG. 1.
FIG. 5A is a cross-sectional view taken along line 5A-5A of FIG. 5.

It has been found advantageous to offset the center of rotation of the articular surface in the volar direction from the vertical center of the head (i.e. in the dorsal-volar plane) which is considered to be essentially the long axis of the 1$^{st}$ metacarpal; in this manner, it is found that the anatomic center of rotation of the joint being repaired can be best reestablished. This offset Q is shown in FIG. 5 for one size; however, it should be understood that the center of rotation offset will be proportionately increased with increasing implant size, i.e. from about 1.1 mm to about 1.7 mm for the largest size of the 4 implant sizes that have been designed. The offset from the flat dorsal surface 23 or the stem is between about 3.5 mm and about 5 mm. The magnitude of the offset Q is placed in perspective when it is compared to the height of the head 13, i.e., the dimension D in FIG. 4, which varies from about 11 mm to about 17 mm. It can thus be seen that the offset is about 10% of the height of the head, and it has been found that offsets of such magnitudes are effective in reproducing desired tendon moment arms, particularly of the abductor pollicis longus (APL).

The width of the head, i.e., the dimension E in FIG. 4, is chosen to preferably be proportionately narrower than the height of the head. It has been found that the desired smooth functioning of the reconstructed joint is achieved if the width is equal to between about 82% to about 87% of the height of the head. By such construction, there is positive avoidance of potential impingement with the 2nd metacarpal and also with the lesser trapezoid bone. The shape is such that the dorsal surface portion 31 of the peripheral surface is essentially flat in a central section equal to about ½ the total width of the head and smoothly transitions into a pair of upper (i.e. dorsal) side surfaces 33 that have very short nearly flat central sections that are aligned at an angle of about 70° to the dorsal surface 31. These surfaces then terminate in a pair of short arcuate lateral surfaces 35 that transition to a pair of lower (i.e. volar) side surfaces 37 that have central flat sections which are aligned at about 45° to the dorsal-volar axis.

The surfaces 37 extend to and flank a short volar arcuate surface 39 of curvature so as to be tangent to the 2 surfaces 37, and the lengths of the lower side surfaces 37 are about twice that of the upper side surfaces 33.

Figure 6:
FIG. 6 is a view of a dislocated human CMC joint with the APL ligament and tendon removed.
Figure 7:
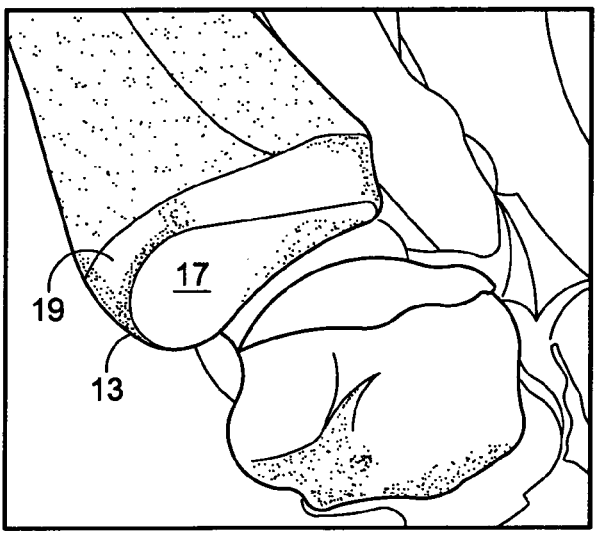
FIG. 7 is a view similar to FIG. 6 showing the joint with the base of the first metacarpal removed and the prosthesis of FIG. 1 implanted in its place.
Figure 8:
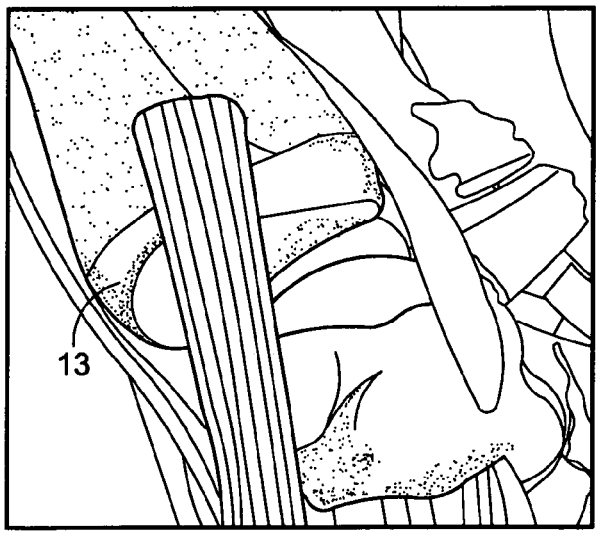
FIG. 8 is a view similar to FIG. 7 with the joint reduced and ligaments and tendon reattached.

The illustrations in FIGS. 6-8 show a hemi joint replacement and the reattachment of the surrounding ligaments and tendons. FIG. 6 depicts the dislocation of the joint between the first metacarpal and the trapezium with the ligaments and tendons removed to better depict the region where the surgery will occur. FIG. 7 shows the first metacarpal with its base removed and replaced by the prosthesis 11, which is installed with the stem fully inserted into the medullary canal that was broached so the dorsal surface of the broach is parallel to the dorsal surface of the metacarpal. Insertion is such that the flat collar 21 is juxtaposed flush with the flat osteotomy on the first metacarpal. FIG. 8 illustrates joint after the replacement and suturing of the ligaments and the APL tendon that surround the joint, following the hemi replacement; it shows that the design of the implant 11 is such that there is no interference with the natural surrounding members at the joint.

Accurate placement of the implant has been found to result in a hemi joint arthroplasty that reestablishes functional joint mechanics, and the features of the implant, particularly the unique shape and proportioning of the head, help preserve the insertion sites for the four ligaments and APL tendon on the base of the metacarpal. Preservation of these soft tissues contributes substantially to joint stability and function. The prosthesis articular surface 17 will accommodate an anatomic range of motion equal to the mean range of active motion of the CMC joint, namely about 53° flexion-extension, about 42° of abduction-adduction, and about 17 degrees of rotation.

To ensure proper and accurate implantation of the implant 11 by the surgeon, an instrument system which includes an awl, a longitudinal axis alignment guide, cutting guide, intramedullary canal broaches, sizing trials and extractors, and a component impactor may be used. During the surgical procedure, the cutting guide instrumentation aids in resection of the first metacarpal bone at the appropriate angle so the flat sub-articular collar 21 of the implant 11 will mate accurately with the cut surface of the bone. Broaches are provided for each size implant so the medullary cavity can be prepared to achieve a tight press fit of the stem 15.

EXAMPLE

It has been found that manufacture of four different sizes of implants 11 having the dimensions set forth in the Table which follows adequately serves the needs of the surgical community. They are provided as a part of a kit, which preferably includes a plurality of broaches of gradually increasing sizes. The heights should be selected so that the change is not greater than about 19% of the next smaller size and preferably at least about 11% larger. The widths should be selected so that they are not greater than about 19% and preferably between about 15% and about 17% larger than the next smaller size.

TABLE

| Size Ref. | A: Adduction/ Abduction Radius | B: Flexion/ Extension Radius | C: Stem Length | D: Head Height | E: Head Width |
|---|---|---|---|---|---|
| CMC-10 | 11.2 | 14.0 | 15.7 | 11.4 | 9.4 |
| CMC-20 | 12.9 | 16.1 | 17.3 | 12.9 | 10.9 |
| CMC-30 | 15.2 | 19.1 | 20.2 | 15.3 | 12.8 |
| CMC-40 | 16.9 | 21.2 | 21.8 | 17.0 | 14.7 |

Dimensions in millimeters

It is found that the provision of these four sizes affords a surgeon an implant to appropriately interface with substantially any native carpal bone of the human thumb. The sizes are constructed so that, at the time of implantation, the surgeon should strive to match the height of the head 13, dimension D, with the dorsal-volar height of the metacarpal osteotomy. By choosing the appropriate implant from the size range available, the head 13 will preferably not extend past the outer margins of the osteotomy.

The implant is designed to articulate against the surface of the trapezium; thus, the most severe wear the implant is likely to experience is expected to occur in patients who have worn through the cartilage on the trapezium because the surface 17 of the implant would then bear against cortical bone. Wear tests are presently demonstrating the excellent wear performance of the pyrocarbon surface bearing on cortical bone. Strength tests on the implant 11 that are similar to strength and fatigue endurance tests which have previously been used to certify other finger joint prostheses, show that the implants are robust, durable and fully capable of supporting the biomechanically demanding loads that are experienced in the CMC joint.

Although the invention has been described with regard to preferred embodiments which constitute the best mode known at this time for carrying out the invention, it should be understood that changes and modifications as would be obvious to one having the ordinary skill in this art may be made without departing from the scope of the invention which is set forth in the claims appended hereto. For example, although the pyrocarbon-coated graphite materials are believed to be the most presently effective materials available for wide application, other strong, durable, FDA-certified materials may be employed for particular applications in the construction of the implants 11.

Particular features of the invention are emphasized in the claims that follow.

The invention claimed is:

1. A hemi joint replacement implant for the base of the first metacarpal of the CMC joint, which implant has a head section and a stem section, said head section having a flat distal collar surface oriented transverse to the stem from which the stem extends, and also having a saddle-shaped proximal articular surface, said proximal surface being convex in a lateral plane and concave in a dorsal-volar plane, and said head section having a peripheral surface which includes a planar central dorsal surface section of a length at least about one-half the width of said head section flanked by a pair of dorsal side surfaces that extend to arcuate lateral surfaces that are connected to a volar arcuate surface.

2. The replacement implant of claim 1 wherein the saddle surface has a convex radius of curvature (RA) in the lateral plane between about 11 mm and 17 mm.

3. The replacement implant of claim 1 wherein the saddle surface has a concave radius of curvature (RB) in the central dorsal-volar plane of the implant between about 14 mm and 22 mm.

4. The replacement implant of claim 1 wherein RB is equal to 125% of RA ±5%.

5. The replacement implant of claim 1 wherein RB is equal to 125% of RA ±1%.

6. The replacement implant of claim 1 wherein said head section flat collar surface from which said stem section extends substantially surrounds the periphery of said stem section.

7. The replacement implant of claim 1 wherein the width of said head section in a lateral direction is equal to between about 82% and about 87% of the height of said head section in a dorsal to volar direction.

8. The replacement implant of claim 1 wherein said planar central dorsal surface section has a length about equal to ½ of the overall width of said head section.

9. The replacement implant of claim 1 wherein said dorsal and volar side surfaces have flat central portions.

10. The replacement implant of claim 1 wherein said volar side surfaces are about twice as long as said dorsal side surfaces.

11. The replacement implant in accordance with claim 1 wherein said flat central dorsal side surface sections are oriented at about 70° to the dorsal-volar plane.

12. The replacement implant according to claim 1 wherein said flat central sections of said volar side surfaces are oriented at an angle of about 45° to the dorsal-volar plane.

13. The replacement implant of claim 1 wherein said implant includes a machined graphite substrate coated about its entire periphery with dense pyrocarbon.

14. The replacement implant according to claim 13 wherein said proximal articular surface of said head section has an average surface roughness of about 8 microinches or less.

* * * * *

UNITED STATES PATENT AND TRADEMARK OFFICE
CERTIFICATE OF CORRECTION

PATENT NO. : 7,641,696 B2
APPLICATION NO. : 10/753108
DATED : January 5, 2010
INVENTOR(S) : Ogilvie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1109 days.

Signed and Sealed this

Sixteenth Day of November, 2010

David J. Kappos
*Director of the United States Patent and Trademark Office*